United States Patent [19]

Mullani

[11] Patent Number: 4,559,597
[45] Date of Patent: Dec. 17, 1985

[54] THREE-DIMENSIONAL TIME-OF-FLIGHT POSITRON EMISSION CAMERA SYSTEM

[75] Inventor: Nizar A. Mullani, Houston, Tex.

[73] Assignee: Clayton Foundation for Research, Houston, Tex.

[21] Appl. No.: 396,098

[22] Filed: Jul. 7, 1982

[51] Int. Cl.⁴ .................... G06F 15/42; G01T 1/20
[52] U.S. Cl. ................... 364/414; 250/363 S
[58] Field of Search .......... 364/414; 250/363 S, 250/366, 369

[56] References Cited

U.S. PATENT DOCUMENTS

| | | | |
|---|---|---|---|
| 3,329,814 | 7/1967 | Anger | 250/61 |
| 3,626,187 | 12/1971 | Laney | 250/71.5 R |
| 3,772,512 | 11/1973 | Laney | 250/366 |
| 3,808,440 | 4/1974 | Petit-Clerc | 250/366 |
| 3,965,353 | 6/1976 | Macovski | 250/366 |
| 3,978,337 | 8/1976 | Nickles et al. | 250/367 |
| 4,071,761 | 1/1978 | Horrocks | 250/369 |
| 4,075,482 | 2/1978 | Perilhou | 250/363 |
| 4,150,292 | 4/1979 | Ter-Pogossian | 250/363 S |
| 4,181,855 | 1/1980 | Horrocks | 250/363 |
| 4,259,578 | 3/1981 | Thompson | 250/363 |
| 4,282,438 | 8/1981 | Nishida et al. | 250/445 |
| 4,284,895 | 8/1981 | Morgan et al. | 250/445 |
| 4,284,896 | 8/1981 | Stonestrom | 250/445 |
| 4,293,912 | 10/1981 | Walters | 364/414 |
| 4,295,047 | 10/1982 | Koga et al. | 250/363 |
| 4,337,397 | 6/1982 | Vacher | 250/363 S |

OTHER PUBLICATIONS

N. Mullani et al., "Feasibility of Time-of-Flight Reconstruction in Positron Emission Tomography," J. Nucl. Med., vol. 21, No. 11, Nov. 1980.
N. Mullani et al., "System Design of Fast PET Scanners Utilizing Time-of-Flight," IEEE Transactions on Nuclear Science, vol. NS-28, No. 1, Feb. 1981.
N. Mullani, "A Review of the Use of Cesium Fluoride and Time of Flight in Positron Tomography".
N. Mullani et al., "Engineering Aspects of PETT V," IEEE Transactions on Nuclear Science, vol. NS-26, No. 2, Apr. 1979.
M. Ter-Pogossian et al., "PETT VI: A Positron Emission Tomograph Utilizing Cesium Fluoride Scintillation Detectors," Journal of Computer Assisted Tomography, vol. 6, No. 1, Feb. 1982.

Primary Examiner—Jerry Smith
Assistant Examiner—Gary V. Harkcom
Attorney, Agent, or Firm—Fulbright & Jaworski

[57] ABSTRACT

An improved sensitivity, multiple detector ring positron emission camera utilizing time-of-flight information to localize the position of a detected annihilation is disclosed. The annihilations detected along each cross-coincidence line between any detector in one ring and a plurality of detectors on the other rings are included in the data of the image slices by determining the nearest measurement position on the plane or interplane slice to the actual location of the annihilation for summing therewith. The positional uncertainty function which characterizes the error in the measurement of the true position of an annihilation along a coincidence line is weighted by an attenuation-uniformity coefficient to determine the contributions to those measurement positions which lie closest to the coincidence line between the detectors detecting the annihilation.

40 Claims, 8 Drawing Figures

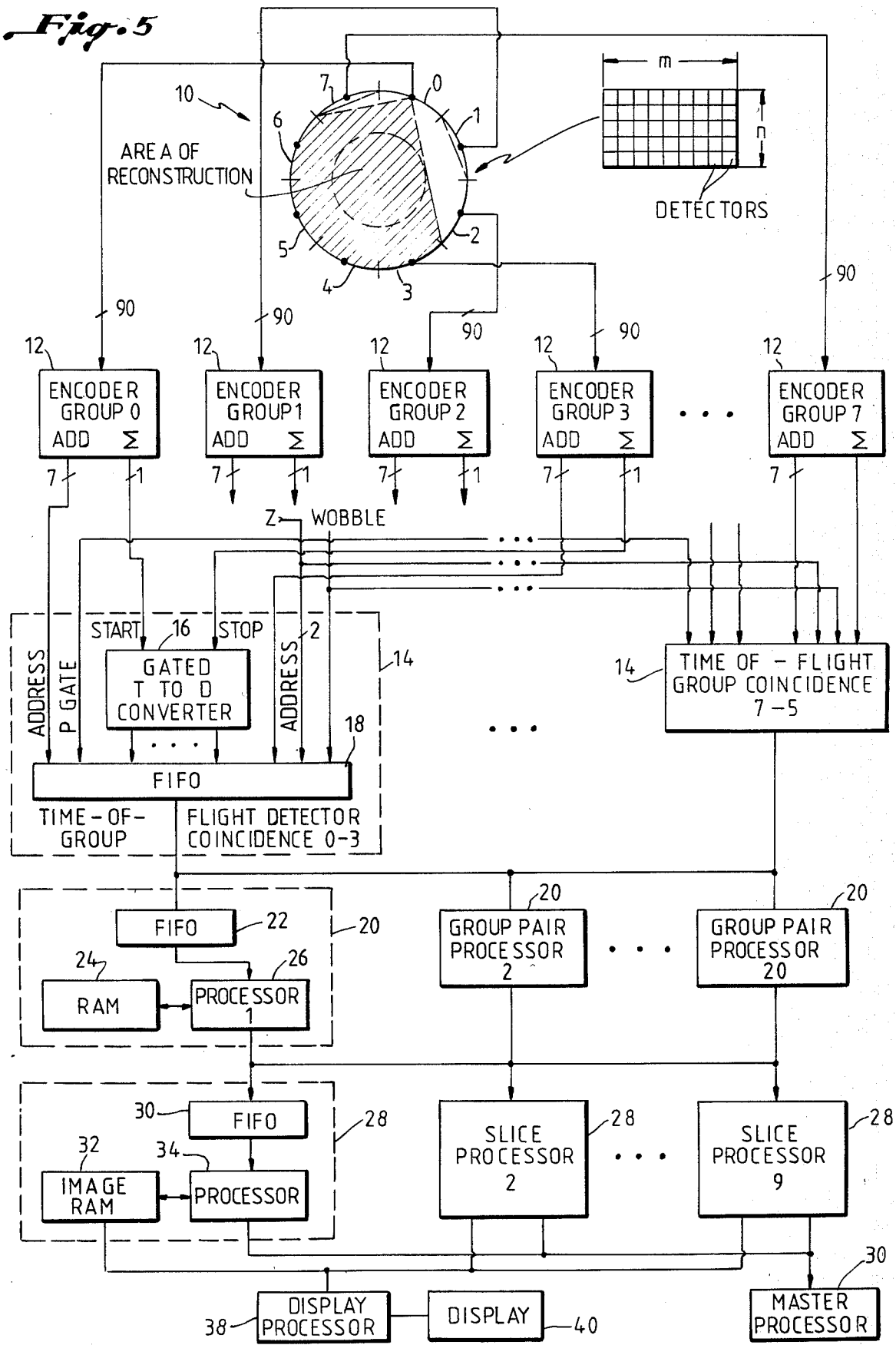

THREE-DIMENSIONAL TIME-OF-FLIGHT POSITRON EMISSION CAMERA SYSTEM

BACKGROUND OF THE INVENTION

This invention relates to positron emission tomography (PET). More particularly, the invention relates to a time-of-flight (TOF) positron emission tomograph (TOFPET) having a substantially improved radiation detection efficiency or sensitivity to positron-electron annihilations in which cross-coincidence lines of detection between scintillation detectors are used in creating image slices through an area of reconstruction.

Position emission cameras are used to scan portions of a human body to develop two-dimensional images of the radioactivity distribution in an area of reconstruction containing a human organ where the images represent a plane slice through the subject. To detect the gamma radiation coming from the area of reconstruction as a result of a positron-electron annihilation, scintillation detectors are provided. In a positron-electron annihilation, two photons of gamma radiation are emitted 180° to each other. By placing a scintillation detector on both sides of the area of reconstruction, it is possible to measure the simultaneous receipt of the two photons, one at each detector, thereby to "detect" the annihilation. Detection of the annihilation is along a line defined by a cylindrically shaped solid angle drawn between the two detectors. This line has a finite circular cross-section because the scintillation detector is not a point source detector, but "sees" radiation received over an area on its detecting surface. This solid angle line then defines the volume within which an annihilation can occur and still be detected by both detectors. As used in the art, this solid angle volume joining the two detectors is called the coincidence line of the detector pair. (As used hereinafter, "coincidence line" is meant to include coincidence lines between detector 180° opposed to each other on the same detector ring and cross-coincidence line between detectors not at 180° to each other whether or not the detectors are on the same ring.)

The simultaneous detection of the two photons is dependent upon the two detectors reacting to receipt of the photons within a predetermined time of each other. If both detectors indicate receipt of a photon within this time window, it is concluded that a "simultaneous" detection has occurred and an annihilation has been "detected." However, the position of the annihilation is not known from this simultaneous detection unless the "time-of-flight" of the two photons is also measured.

In conventional PET cameras, the number of annihilations registered in a coincidence line is integrated for a fixed time. For each coincidence line through the area of reconstruction, one data point of the area of reconstruction is obtained. To obtain additional points, additional coincidence lines must be created by adding additional detectors around the area of reconstruction. Because of the integration time, it requires a substantial period of time to scan the area of reconstruction, and accordingly, requires a patient to be in the camera for an extended length of time.

With recent advances in fast radiation detectors, the measurement of the time-of-flight of the two photons emitted from a positron-electron annihilation has become possible. The gamma photons from an annihilation travel at the speed of light, and by measuring the time difference in the detection of these two photons by the detector pair and using a simple geometrical relationship, the distance of the annihilation from either one of the detectors along the coincidence line can be calculated. In other words, the position of the annihilation in the area of reconstruction as measured along the coincidence line can be obtained. Thus, one coincidence line can yield several detected annihilations at various points along the coincidence line which thereby improves the quality of the resulting images.

However, even with fast radiation detectors, it is not possible to exactly determine the location of the annihilation along the coincidence line. For example, a one nanosecond time difference in the measured time-of-flight corresponds to a 15 cm spatial difference in the location of the annihilation along the coincidence line. Unfortunately, the positional information has an associated uncertainty which is dependent on the statistical limitations of the detectors to precisely measure the true time difference between receipt of the two photons. For a positron source located between two detectors, a gaussian shaped distribution of time-of-flight measurements is obtained, with the mean located at the source of positrons. This function is commonly referred to as the positioning uncertainty function, and is described by a single parameter obtained from the width of the uncertainty function measured between the half maximum points (FWHM) of the symmetrical gaussian shaped curve.

If the uncertainty in the location of the annihilation could be reduced to less than 1 cm, it would be possible to construct the radioactivity distribution in the area of reconstruction by simply counting the number of annihilations that occured at selected measurement positions along the coincidence line. However, because of the positional uncertainty, a reconstruction process must be utilized which, unfortunately, tends to amplify the noise in the resulting image. Present scintillation detectors, such as cesium fluoride, have a positional uncertainty of less than 500 picoseconds which results in a FWHM of 7.5 cm spatial uncertainty. Such a large uncertainty does not permit direct localization or the annihilation, but does permit a reconstruction process which achieves an improved image quality over standard PET cameras.

The coincidence detection of the two gamma photons is related to various factors, such as the solid angle represented by the two detectors, the detection efficiency of the scintillator detectors, and the attenuation of the gamma ray within the object. The tissues of the human body, for example, attenuate the gamma photons. For a typical pair of detectors in a whole body scanner, the number of gamma photons impinging on each detector may be as high as 50,000 per second. Out of these 50,000, no more than 100 (0.2%) will be detected in coincidence by the electronics. The coincidences which are detected are not all "true" coincidences, but have two other components. These two components are called "scatter" and "randoms."

Scatter is caused by the interaction of the gamma photons with the tissue matter of the human body, ano results in a secondary gamma which has lost its direction and some of its energy. Randoms are caused by the chance detection of two unrelated gammas in the coincidence electronics. Typically in conventional systems, the contribution of the scatter and randoms to the total coincidence events detected may be 20% for the scatter and 10–30% for the randoms. This leaves at least 50% of the total coincidences detected as "true" coincidences. Thus, the detection efficiency of "true" coincidences from a typical patient for one detector pair may be as low as 0.1% for all the gamma photons impinging on each detector.

Prior-art PET cameras have attempted to solve this low detection efficiency by adding detectors around the patient such that the number of detector pairs in coincidence is increased. A single ring of detectors around the patient may have as many as 1,000 different detector pairs in coincidence by making each detector in coincidence with 20 or more detectors facing it. In this manner, a single detector will have a fan shaped area of coverage as defined by the coincidence lines between the detector and the 20 or so detectors facing it on the opposite side of the area of reconstruction.

The coincidence line between two detectors that are not 180° opposed to each others is called a cross-coincidence line. With this technique of "cross-coincidence," the number of "true" coincidences which are detected by each detector becomes approximately 2% of the detected gammas. For a ring of detectors operating in cross-coincidence, the total efficiency for the detection of coincidences is increased by a factor of about 1000 over that for a single pair of detectors. A detector ring operating with coincidence lines or with cross-coincidence lines, measures the radioactivity distribution through the area of reconstruction as a plane slice defined by the detector ring.

Another technique used in prior-art PET cameras has been to add more rings of detectors, positioned side-byside, such that multiple slices of the patient are collected simultaneously. Since the radioactivity injected into a patient defuses throughout an organ of interest, it is more efficient to collect as much of the information from that organ as possible at the same time. This increases the overall detection efficiency and reduces the total scan time and/or the dose to the patient. By operating some of these rings of detectors in cross-coincidence such that coincidences are allowed between detectors on different rings, and making some approximations, the prior art has been able to obtain additional slices through the area of reconstruction.

A state-of-the-art camera using four rings of detectors around the patient is able to obtain four straight-on slices defined by the detector rings and three interplane slices located between the four major detectors rings. The major approximation made in this system is that two cross-plane coincidences between detectors on adjacent rings can be summed to produce another image plane in between the two rings. However, the interplane slices created in this manner are not uniform in resolution throughout the region of interest, but rather produce a conical shape of coverage of the organ. A high quality interplane image reconstructed from this conical shaped data is not possible. Additionally, only a small number of the total possible cross-plane coincidence lines between the multiple detector rings are used to reconstruct the plane images.

Thus, it would be advantageous to provide a positron emission camera in which all of the possible cross-plane coincidence detections can be used in the reconstruction process thereby increasing the radiation detection efficiency or sensitivity of the camera. It would also be advantageous to provide a positron emission camera where the images formed on the interplane slices from data obtained on the cross-coincidence lines between detector rings are of the same quality and kind as are obtained for the plane slices defined by the detector rings. It would also be advantageous to provide a positron emission camera that reduces the time to create high quality three-dimensional images of an organ of a patient thereby reducing the time the patient must be in the camera. It would also be advantageous to provide a positron emission camera having an increased sensitivity thereby reducing the dosage of the radioactive substance to the patient.

SUMMARY OF THE INVENTION

In accordance with the present invention, a method of improving the radiation detection efficiency of a time-of-flight positron emission camera is disclosed. The positron emission camera includes a plurality of detector rings positioned side-by-side around an area of reconstruction where each ring contains a plurality of scintillation detectors pointed at the area of reconstruction to detect radiation therefrom. Each detector in each ring has an opposed detector 180° therefrom to define a detector pair for detecting the two photons emitted along a coincidence line defined by the coincidence solid angle cylindrical line connecting each detector from a positronelectron annihilation occurring in the area of reconstruction. Each detector ring also defines a plane slice through the area of reconstruction with an interplane slice defined as all equidistant points located between any two adjacent detector rings as measured from either plane slice.

The method includes the step of determining the time-of-flight of each annihilation detected along a coincidence line. Also included is the step of determining the position of each annihilation detected in each plane slice from the time-of-flight measurements of the annihilations detected along the coincidence lines between detectors on the ring defining the plane slice. A further step is included of determining from the time-of-flight information the position for each annihilation detected along each coincidence line involving detectors on different rings. The method includes the final step of forming the total detected annihilations which have occurred at each measurement position in each plane and interplane slice by (1) summing with the annihilations detected in each position in each plane slice the annihilations detected on coincidence lines involving detectors on different rings where the position of the annihilations so detected are within a predetermined distance of the position in the plane, and (2) summing for each position on an interplane slice the annihilation detected on coincidence lines involving detectors on different rings where the position of the annihilations so detected are within a predetermined distance of the position in the interplane thereby to increase the detection efficiency of the camera.

In another embodiment of the invention, a method of improving the radiation detection efficiency of a time-of-flight positron emission camera having a plurality n of detector rings positioned side-by-side around an area of reconstruction is disclosed. Each ring has a circumference and each contains a plurality of scintillation detectors which are positioned around its circumference to detect radiation occurring from the area of reconstruction along a coincidence line defined by the coincidence solid angle cylindrical line connecting a detector with another detector. The plurality of detectors on the detector rings are divided into a plurality of detectors groups with each group having $m \times n$ detectors where m represents a number of adjacent detectors on the same ring.

The plurality of detector groups define therebetween a plurality of group coincidence lines where each group coincidence line connects a first and a second group and includes the coincidence lines between each detector, taken one at a time, in the first group and every detector in the second group. Each detector in the first group together with a detector in the second group defines a detector pair for detecting the two photons emitted along the coincidence line therebetween. Each detector ring defines a plane slice through the area of reconstruction with an interplane slice defined as all equidistant points located between any two adjacent detector rings as measured from either plane slice and where each slice has an array of measurement points.

The method includes the step of determining the time-of-flight of the annihilations detected along the group coincidence lines where each determination includes a determination of which coincidence line in the group coincidence line detected the annihilation. The method also includes determining from the time-of-flight information the location of each detected annihilation along a coincidence line. Also included is the step of determining for each detected annihilation location, the nearest measurement position on the nearest plane or interplane slice to the location of the annihilation. The method also includes as a final step, forming the total detected annihilations for each measurement position in each plane and interplane slice by summing each detected annihilation with the number of annihilations already obtained at the nearest measurement position to the location of the annihilation thereby to obtain a greater detection efficiency for the camera.

In a narrower aspect of the invention, the step of determining for each detected annihilation the nearest measurement position on a plane or interplane slice includes the step of converting the position of each detected annihilation along a coincidence line into orthogonal components comprising (1) a perpendicular distance of the annihilation as measured from the plane slice which includes one of the detectors defining the coincidence line where the detector used in defining the plane slice is referred to as a reference detector and the plane so defined is referred to as the reference plane for the annihilation, and (2) a horizontal distance of the annihilation in the reference plane as measured along a projection of the coincidence line onto the reference plane from the reference detector. Also included is the step of determining for each annihilation the plane or interplane slice that is nearest the annihilation as measured by the perpendicular distance from the reference plane of the annihilation. Finally, the nearest measurement position to the annihilation in the nearest plane determined in the previous step is determined.

In another aspect of the invention, a time-of-flight positron emission camera having an improved radiation detection efficiency for detecting the photons emitted by an electron-positron annihilation along a line of coincidence and for locating the annihilation within an area of reconstruction is provided. The camera includes a plurality n of detector rings positioned side-by-side around the area of reconstruction where each ring contains a plurality of scintillation detectors for detecting radiation therefrom. The plurality of detectors on the detector ring are divided into a plurality of detector groups where each group includes m×n detectors where m represents a number of adjacent detectors on the same ring. The plurality of detector groups define therebetween a plurality of group coincidence lines where each group coincidence lines includes a first and a second group, and also includes the coincidence lines between each detector, taken one at a time, in the first group and every detector in the second group, where each detector in the first group together with a detector in the second group defines a detector pair for detecting the two photons emitted along a coincidence line defined therebetween.

Also included is a plurality of time-of-flight detectors for measuring the time difference between the simultaneous detection of the photons from an annihilation by a first and a second detector group having a group coincidence line therebetween, where the simultaneous detection occurs when the detected photon by one detector in the first group is within a predetermined time interval of the detection of a photon by another detector in the second group.

A plurality of group-pair processors, one processor associated with each of said time-of-flight detectors are included for determining the location of each detected annihilation relative to the nearest measurement position in the slice nearest to the location of the annihilation. The location of each annihilation includes the angle of the coincidence line to the plane slices, and an attenuation-uniformity coefficient representative of the weighting function to be applied to the positional uncertainty function to obtain partial contributions to be added to those measurement positions spanned by the uncertainty function as measured from the most likely position of the detected annihilation.

A plurality of slice processors, responsive to the group-pair processors, are provided for generating the number of annihilations detected at each measurement position in each plane and interplane slice. Each annihilation produces a partial contribution to the number of detected annihilations at a plurality of measurement positions which lie closest to the coincidence line of the detected annihilation in accordance with the location uncertainty function and the attenuation-uniformity coefficient. Finally, a display means is provided for displaying a two-dimensional image of the area of reconstruction as a plane slice through the area of reconstruction from the number of annihilation obtained at each measurement position in a plane or interplane slice.

In a narrower aspect of the invention, each time-of-flight detector includes a first encoder means associated with a first detector group for detecting when a detector in the first detector group has detected a photon from an annihilation. The first control encoder means generates a start conversion signal in response to a detected photon. A second encoder means is associated with a second detector group where the first and second detector groups define therebetween a group coincidence line. The second encoder means detects when a detector in the second detector group has detected a photon from an annihilation and generates a stop conversion signal in response to a detected photon. A time-to-digital converter is included and responds to the start and stop conversion signals for measuring the time difference between the detection of a photon by the first group and the detection of a photon by the second group. The time difference measured represents the time-of-flight of the annihilation along the coincidence line between the detectors which detected the photons in said first and second groups if the time difference is less than a predetermined amount.

In a narrower aspect of the invention, the camera further includes a means for wobbling during detection of the annihilations the plurality of detector rings such that the position of each detector relative to the area of reconstruction varies in a known manner thereby increasing the sampling of the area of reconstruction without longitudinal movement of the rings.

In yet another narrower aspect of the invention, the camera further includes means for indexing the plurality of detector rings in predetermined increments longitudinally relative to the area of reconstruction thereby increasing the number of measurement slices through the area of reconstruction without increasing the number of detector rings.

BRIEF DESCRIPTION OF THE DRAWINGS

For a fuller understanding of the invention reference should be had to the following detailed description taken in conjunction with the accompanying drawings in which:

FIG. 5 is a schematic block diagram of the positron emission camera of the present invention;

Similar reference numerals refer to similar parts throughout the several views of the drawings.

DETAILED DESCRIPTION OF THE PREFERRED EMBODIMENT OF THE INVENTION

Figure 1:
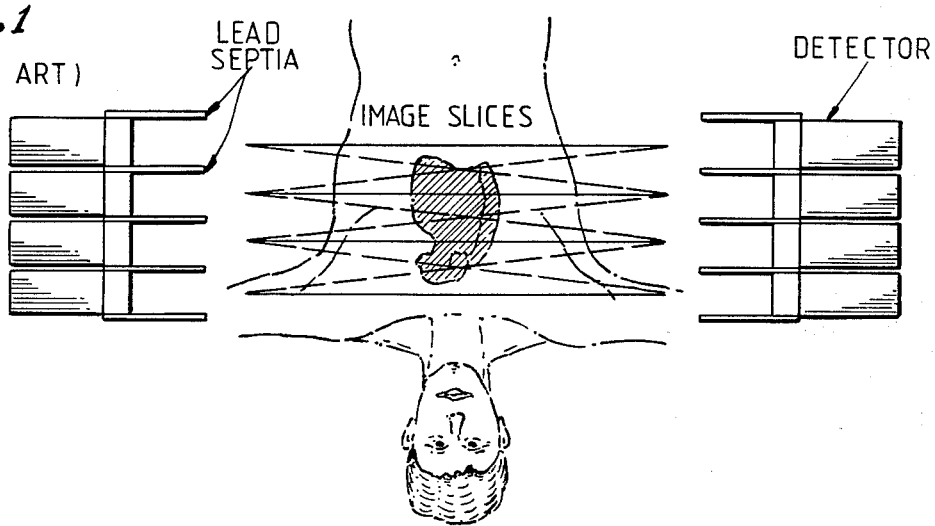
FIG. 1 is a pictorial presentation of a typical prior-art positron emission camera in which cross-coincidence lines between detectors on different rings are summed to produce an image of the region in between the two plane slices.

Referring now to the figures and first to the prior-art positron emission camera shown in FIG. 1, four rings of detectors are illustrated around a patient for collecting four plane slices (straight-on slices) and three interplane slices. The detector arrangement illustrated in FIG. 1 represents a plane through the detector rings and illustrates only those detectors that are 180° apart on their respective rings. Extending inwardly and positioned between each detector ring is a plurality of shielding extensions called "lead septa." The lead septa rings act to shield the detectors from radiation at high angles of incidence from reaching the detectors. In this manner, the detectors are responding to radiation generally emanating from the area of reconstruction where the patient has been positioned.

In the prior-art PET camera of FIG. 1, the major approximation made in this system is that the detected annihilations along two cross-coincidence lines, shown as dotted lines in the Figure, are summed together in accordance with prior-art techniques to obtain an interplane slice through the area of reconstruction located between the two detector rings. However, the interplane slices created in this manner are not uniform in resolution throughout the region of interest, but represents a conical detection area. In accordance with this approach, only a limited number of cross-coincidence lines are used in the detection process even though a larger number of cross-coincidence lines exist.

Figure 2:
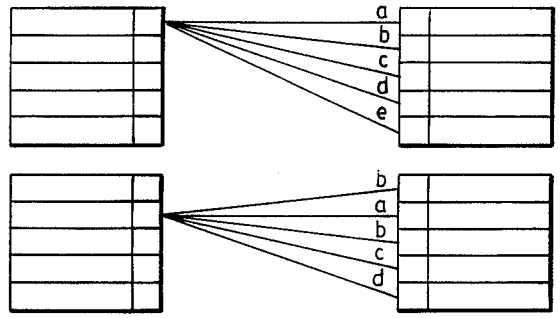
FIG. 2 is an illustration of the cross-coincidence lines for the interplane data in accordance with the present invention.

Turning now to FIG. 2 which illustrates the total possible cross-coincidence lines for a typical prior-art multi-ring positron emission camera, it can be seen that each detector (a reference detector) in the illustrated two-dimensional case, will have five possible coincidence lines. Where the other detector that defines a detector pair with the reference detector is on the same detector ring as the reference detector, the coincidence line is the straight-on coincidence line a. Each cross-coincidence line between the reference detector and a detector on an adjacent ring is labeled b. For each detector ring further away from the ring containing the reference detector, the cross-coincidence lines are labeled c, d, e, etc.

To the extent that the lead septa rings permit, the cross-coincidence lines illustrated in FIG. 2 represent coincidence lines along which an annihilation can be detected using the time-of-flight measurement technique.

Figure 3:
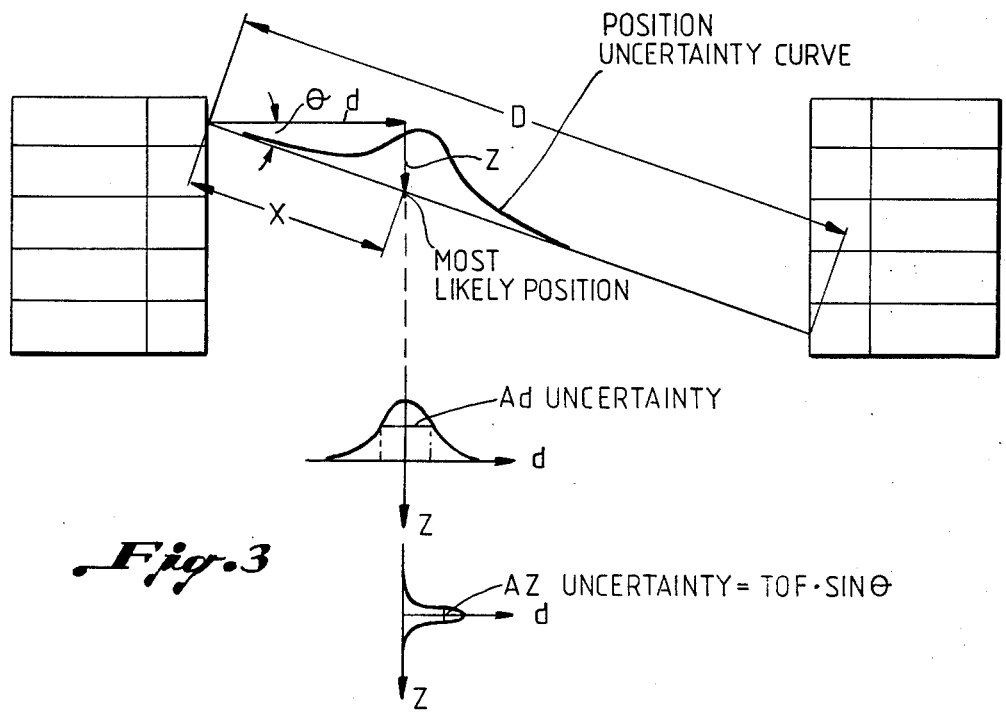
FIG. 3 is a diagrammatic illustration of the positional uncertainty function resulting from the time-of-flight measurement along coincidence lines.

As previously discussed, each positron-electron annihilation produces two gamma photons travelling in opposite directions at the speed of light. By measuring the time difference in the detection of these two photons by a pair of detectors, one photon by each detector, it is possible using a simple geometrical arrangement to obtain an estimate of the actual position of the annihilation. This estimate of the position of the annihilation along a coincidence line has an uncertainty associated with it. This uncertainty is a result of the limitations of the detectors and is represented by a gaussian shaped distribution of the time-of-flight measurements about the most likely position (the mean) located at the source of of the photons. FIG. 3 is an illustration of this positional uncertainty curve about the most likely position of an annihilation detected along a cross-coincidence line. The curve is the same where the two detectors defining the coincidence line are on the same detector rings.

The distance between the two detectors defining the cross-coincidence line is given as D. The distance from one of the detectors (the reference detector) is represented by the variable x. Since both of the photons emitted from the annihilation travel at the speed of light, the following relationship obains;

$$TOF = \frac{2x - D}{c},$$

where TOF is the time difference between receipt of the photon by the reference detector and the receipt of the other photon by the other detector.

The above relationship would hold true for the ideal case in which the detectors respond instantaneously to receipt of the photons. But since the detectors do not exhibit this ideal response time, there is a finite amount of electronic delay introduced by each detector between the time a photon is received and the time that that event is indicated. Thus, for each detector pair on a coincidence line, a measurable time delay ($\Delta$) is contained in each detected annihilation TOF measurement, and this delay may vary from detector pair-to-detector pair. To obtain the true position of a detected annihilation, this time delay $\Delta$ must be compensated for by the image reconstruction process. Therefore, the above expression may be rewritten to express the true TOF measurement $$TOF = \frac{2x - D}{c} + \Delta.$$

Given the measured time-of-flight position and a known cross-coincidence line represented by the angle $\theta$, it is possible to compute the position of the annihilation in a slice direction (the z direction) relative to the slice of the reference detector. This is shown in FIG. 3 by the perpendicular distance z measured from the plane of the reference detector down to the position of the annihilation on the cross-coincidence line.

Referring to FIG. 3, the positional uncertainty curve is illustrated along the cross-coincidence line with the most likely position, the peak of the curve, occurring at the position of the annihilation. This positional uncertainty curve can be resolved into two orthogonal curves. The curve component in the plane slice containing the reference detector represents the distance d from the reference detector along a line resulting from a projection of the cross-coincidence line onto the plane containing the reference detector. The uncertainty in the actual length of the distance d in the plane slice containing the reference detector is represented by the parameter $\Delta d$ as measured from the FWHM.

In a similar manner, the component of the uncertainty curve in the z direction illustrates the uncertainty $\Delta z$ in the determination of the z perpendicular distance. In a multi-ring positron emission camera, the angle $\theta$ is small. Therefore, the $\Delta z$ uncertainty in the z direction likewise is small and is given by the following expression:

$$\Delta z = TOF \cdot \sin \theta.$$

This resulting uncertainty in the z direction is small, as can be seen in FIG. 3.

As an example of the uncertainty in the determination of the perpendicular dimension z for an annihilation occurring on a cross-coincidence line in a typical positron emission camera having detectors with an uncertainty of 9.0 cm FWHM, 144 detectors per ring at a diameter of 99 cm and a side-by-side detector-to-detector distance of 2.16 cm, the values of $\Delta z$ and $\Delta d$ are shown in TABLE 1.

TABLE 1

| Coincidence line | Coincidence angle | Number of the Coincidence line | Positioning error $\Delta z$ | Positioning error $\Delta d$ |
|---|---|---|---|---|
| a | 0 | 5(a) | 0 cm | 9 cm |
| b | 1.25 | 8(b) | 0.196 | 8.998 |
| c | 2.5 | 6(c) | 0.393 | 8.99 |
| d | 3.75 | 4(d) | 0.589 | 8.98 |
| e | 5.0 | 2(e) | 0.784 | 8.966 |

Because of this small uncertainty in the position of the annihilation in the z direction, it is possible to locate with a high degree of certainty each annihilation relative to the plane or interplane slices. Thus, in accordance with the invention, annihilations detected along cross-coincidence lines can be included in the measurement data for the plane or interplane slices through the area of reconstruction. As embodied in the present invention, the cross-coincidence lines are used with time-of-flight measurements to determine the position of detected annihilations along the cross-coincidence lines, and from these measured positions, the image plane (plane slice or interplane slice) in which the data belongs. Once the measurement position in the closest image plane to the position of the annihilation has been determined, the annihilation is then included in the other data for that image in the reconstruction process. The inclusion of each detected annihilation into the data of the plane slices is not done, one detected annihilation to one measurement position.

Because of the uncertainty associated with the exact position of each detected annihilation, the better reconstruction process involves distributing each detected annihilation to several measurement positions which are spanned by the positional uncertainty function along the coincidence line, where the partial contributions determined from the uncertainty function are added to the closest measurement position in the planes nearest to the location of the partial contribution component. A more detailed explanation of this function is given below with respect to FIG. 6. This process of including partial contributions of the annihilations detected along cross-coincidence line is illustrated in FIG. 4 and shows how the positional information for an annihilation along a cross-coincidence line is included in the data for various plane and interplane slices.

Figure 4:
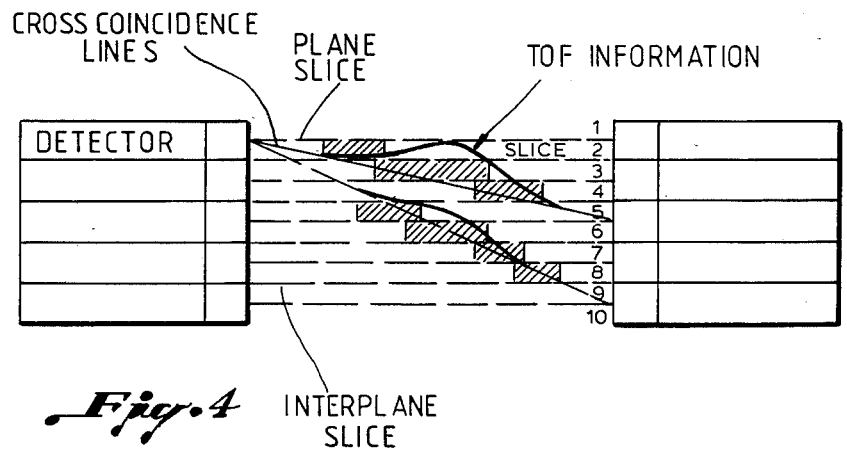
FIG. 4 is an illustration of the contribution of annihilations detected along cross-coincidence lines to the interplane slices by time-of-flight localization according to the present invention.

Referring now to FIG. 4, a two-dimensional illustration of the contribution of the cross-coincidence lines to the image slices according to the present invention is shown. The detector arrangement illustrated in FIG. 4 is for a five-ring detector gantry in which five straight-on plane image slices are labeled slice 1, 3, 5, 7, and 9, and four interplane image slices are labeled 2, 4, 6, and 8. The positional uncertainty curves for two cross-coincidence lines are shown. Each detected annihilation is distributed over multiple image slices. Thus, a single annihilation detected along a coincidence line may contribute to the total data on more than one image slice.

Using the method of the present invention to utilize all of the cross-coincidence lines in a positron emission camera, it is possible to increase the sensitivity or the radiation detection efficiency of the camera by a substantial amount. This increase in camera sensitivity depends among other things upon the number of rings of detectors in the detector gantry. For a five-ring system operated in accordance with the invention, an estimated increase of a 1.92 over that of a conventional PET camera is possible. Additionally, the present invention is able to obtain a more uniformed spatial response from slice-to-slice then is presently obtained in conventional PET cameras. Because more coincidence lines view the region of interest, the sensitivity of the central slices is expected to be as much as three times as high as the outer straight-on slices. The following TABLE 2 illustrates the maximum sensitivity improvement in the TOF interslice positioning as compared to a conventional PET scanner by interslice coincidence utilization.

TABLE 2

| | 1 | 2 | 3 | 4 | 5 | 6 |
|---|---|---|---|---|---|---|
| Number of detector rings | 1 | 2 | 3 | 4 | 5 | 6 |
| Number of cross-coincidences | 1 | 4 | 9 | 16 | 25 | 36 |
| Number of cross-coincidences used in PET | 1 | 4 | 7 | 10 | 13 | 16 |
| Improvement factor with TOFPET positioning | 1 | 1 | 1.28 | 1.59 | 1.92 | 2.22 |

The improvement factor of the present invention over a typical PET scanner of the prior art presented in TABLE 2 was obtained with a system where no lead septa are used between the detector planes (see FIG. 2). This arrangement, however, introduces a substantial amount of scatter in the data and may not be acceptable for a clinically usable system. Using the equations developed by S. E. Derenzo for a true and scattered radiation, as presented in his article articled "Method for Optimizing Side Shielding in Positron-Emission Tomographs and for Comparing Detector Materials," appearing in the Journal of Nuclear Medicine, Volume 21, No. 10 at pages 971–76, it is possible to determine the fraction of events which are scattered and accepted by the detector. It is found that this fraction is proportional to the slice thickness and inversely proportional to the septa length. Thus, the extension of the septa length towards the patient from the detector can reduce these scattered events by a substantial amount. Unfortunately, this also reduces the sensitivity for the cross-coincidence lines since the detector aperture is closed down for the higher order cross-coincidence lines. The relationship between septa length and the detection efficiency for each one of the cross-coincidence lines is shown in the following TABLE 3, where a, b, c, d, and e represent the cross-coincidence lines shown in FIG. 2 with a representing the straight-on coincidence line and e representing the highest cross-coincidence line.

TABLE 3

| Septa length cm | Coincidence line efficiency | | | | |
|---|---|---|---|---|---|
| | a | b | c | d | e |
| 7.0 | 1.0 | 0.89 | 0.82 | 0.73 | 0.62 |
| 10.0 | 1.0 | 0.86 | 0.74 | 0.57 | 0.40 |
| 12.5 | 1.0 | 0.83 | 0.64 | 0.42 | 0.22 |
| 15.0 | 1.0 | 0.79 | 0.54 | 0.27 | 0.09 |
| 20.0 | 1.0 | 0.69 | 0.31 | 0.08 | 0.0 |

For the preferred embodiment of the present invention, the septa length is chosen at 12 cm since it still offers good sensitivity and yet only minimizes the cross-coincidence lines which have the largest positioning error in the z direction to begin with. To further reduce the scatter, the detectors can be moved back further from the area of reconstruction so that longer side shielding from the detectors to the patient can be added. This aids in reducing the detectors acceptance angle for the scattered radiation arriving from the patient's body. For a TOFPET geometry of 12 cm septa lengths, 99 cm diameter detector rings, 144 detectors per ring, 2.16 cm side-by-side Turning now to FIG. 5 which illustrates a block diagram of the measurement circuits of the TOFPET camera according to the present invention, the detector gantry 10 is shown divided into a plurality of detected groups labeled 0 through 7. Each detector group is divided into an array which is m × n in size. The number m represents a plurality of detectors on a single ring and the number n represents the number of detector rings in the detector gantry 10. In the presently preferred embodiment, m is 18 and n is 5, totaling 90 detectors in each detector group.

In accordance with the invention, each detector in a detector group "sees" every other detector in a plurality of detector groups opposed to it. This is illustrated in FIG. 5 with respect to detector group 0 which sees detector groups 2–6. Not only does each detector in a ring of group 0 see the detector located 180° therefrom on the same ring, but that detector sees each detector on each ring contained in each group 2–6. Thus, each detector in a given detector group sees a three-dimensional volume of the area of reconstruction as defined by the possible cross-coincidence lines between the detector and each detector in the groups that it "sees." For purposes of discussion, each detector group sees another detector group across a group coincidence line defined as all of the coincidence lines between each detector in one group, taken one at a time, and every other detector in the other group.

In accordance with the present invention, the time-of-flight information for a simultaneous detection of the two photons along a coincidence line for a positron-electron emission is to be measured. The measurement of the time-of-flight of a detected annihilation is described detector-to-detector separation, and five detector rings, TABLE 4 lists the relative efficiency of each interplane coincidence line and the percentage of data it contributes to the total sensitivity of the camera. The improvement in overall sensitivity of the camera in accordance with the present invention as compared to a conventional nearest neighbor cross-utilization technique is a factor of 1.6, with the central slices being three times higher in sensitivity than a straight-on slice.

TABLE 4

| Cross-Coincidence | Number of lines | Efficiency | % of Total Data |
|---|---|---|---|
| (a) | 5 | 1.0 | 33% |
| (b) | 8 | .83 | 27.46% |
| (c) | 6 | .64 | 25.41% |
| (d) | 4 | .42 | 11.11% |
| (e) | 2 | .22 | 2.92% |

The foregoing discussion of the present invention has been with respect to the simple geometrical arrangement for the utilization of cross-coincidence lines in a two-dimensional arrangement where the two detectors that define a coincidence line, straight-on or cross-coincidence line, are represented by detectors disposed 180° from each other and contained on a plane which passes through the center of the detector rings. The following discussion will describe the present invention with respect to the preferred embodiment of a TOFPET camera where cross-coincidence lines are measured in a threedimensional arrangement in which a cross-coincidence line may exist between detectors on different rings and where the detectors are located at angles other than 180° from each other, as follows: Each detector in each group is connected to an encoder 12 which functions to generate an active signal which functions either as a start or a stop conversion signal to a time-of-flight detector 14 associated with a pair of the encoders 12. For the present invention, there are eight encoders 12 and twenty time-of-flight detectors 14. Since each detector group sees five opposed detector groups, there are twenty non-redundant group coincidence lines possible. Accordingly, twenty time-of-flight detectors 14 are provided for detecting annihilations occurring along the twenty group coincidence lines.

Each encoder 12 receives ninety signal lines, one from each detector in a detector group. A scanning process is performed in each encoder in which each signal line from the detector group is sequentially examined to determine if it is receiving a photon of radiation. If a detector is "active," the encoder 12 will output an active signal and a 7-bit address which uniquely identifies which of the ninety detectors is generating the active signal. To measure the time difference between the simultaneous detection of two photons, each group coincidence line arbitrarily selects one of the groups as a reference group to generate a start conversion signal to begin the measurement of the time difference. The other group defining the group coincidence line will be used to stop the time measurement.

FIG. 5 illustrates the time-of-flight detector 14 between the group coincidence line of group 0 and 3. The active signal coming from encoder 12 associated with group 0 is used as the start conversion signal to a gated time-to-digital converter 16. The active signal coming from encoder 12 associated with group 3 is used as the stop conversion signal. The output from the time-to-digital converter is a 9-bit digital code of the TOF measurement that is loaded into a FIFO 18 along with the encoder 12 address for the detectors that produce the start and stop active signals. Other information such as the wobble and translational positions of the detector gantry 10 is also loaded into the FIFO 18. The wobble and longitudinal positioning of the detector gantry 10 is discussed in more detail below.

The measurement of the time-of-flight for each annihilation detected along each of the twenty group coincidence lines are obtained in the manner as just described.

The information in the FIFOs 18 of the time-of-flight detectors 14 are connected via a common bus to a plurality of group-pair processors 20. There is a group-pair processor 20 associated with each time-of-flight detector 14. Each of the group-pair processors 20 perform a coordinate transformation to determine the x, y and z location of the annihilation event within the measurement space of the area of reconstruction, and to obtain the angle of coincidence (θ) along with an associated attenuation-uniformity coefficient. The attenuation-uniformity coefficient is used to distribute the contribution of the detected annihilation among several measurement positions in the plane and interplane slices, rather than having a single contribution of the annihilation to the image data occur at its most likely position.

Each group-pair processor 20 includes a FIFO buffer memory 22 for buffering the data from the time-of-flight detectors 14, a microprocessor 26 and a random access memory unit 24. A very fast data bus interconnects each of the group-pair processors 20 to a plurality of slice processors 28. For the presently preferred embodiment, there are twenty slice processors 28 which are able to generate from nine to twenty image slices through the areas of reconstruction depending on the data collection mode.

Each slice processor 28 includes a FIFO buffer memory 30 for buffering the data from the group-pair processors 20. Also included in each slice processor 28 is a microprocesser 34 and an image random access memory unit 32. The slice processors 28 convert the geometrical location of each annihilation into contribution components in accordance with the positional uncertainty function and the attenuation-uniformity coefficient to create the data for each of the image slices. When the image data is complete, a display 40, responsive to a display processor 38, can display either two-dimensional images from the slice data or a three-dimensional image including the information from all of the slices.

Also connected to each of the slice processors 28 is a master processor 36 that assists with computations for system calibration as well as establishing the interface between an operator and the TOFPET camera. Each of the processors 26 and 34 for the present invention are fast microprogrammable bit-slice devices available from Advance Micro Devices as their Model 2900, organized into a 24-bit architecture with a cycle time of less than 200 nsec. Additionally, individual 16-bit hardware multiply chips operating in parallel with each processor 26, 34 are incorporated to speed up the computations required to locate the position and to determine the contribution of each annihilation to the image data positions.

Figure 6:
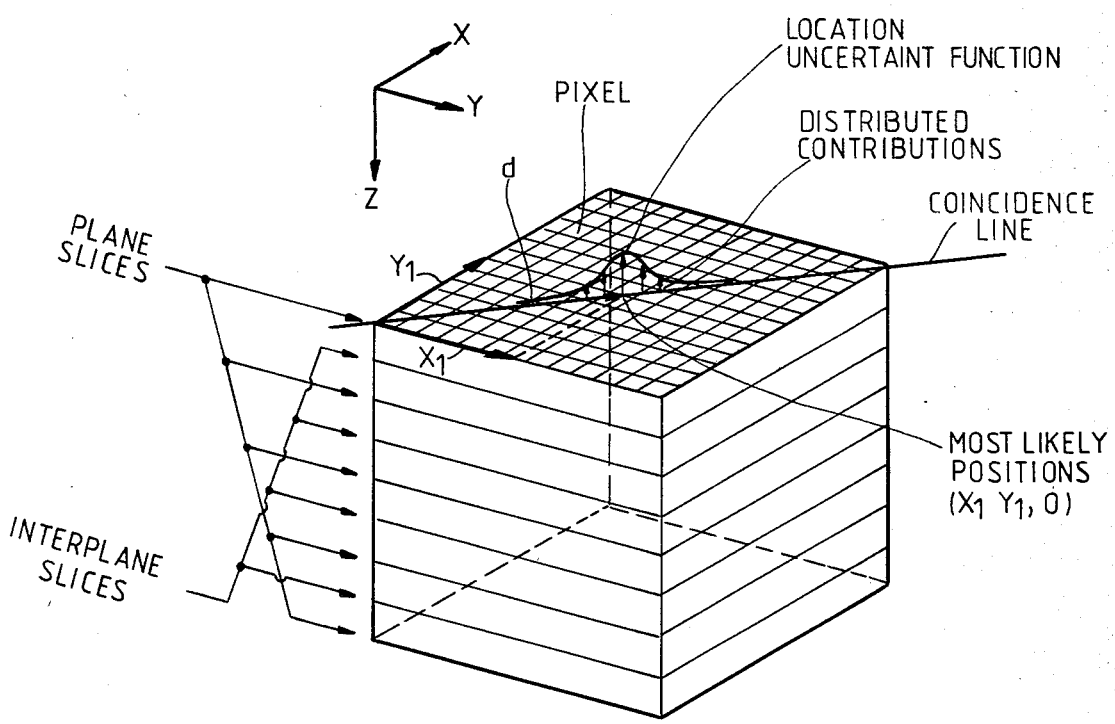
FIG. 6 is an illustration of the sampling space comprising the plane and interplane slices through the area of reconstruction, and illustrates the distributed contributions of a detected annihilation to the total counts obtained at each measurement position in the measurement space.

Turning now to FIG. 6 there is illustrated the measurement space of the area of reconstruction in accordance with the invention. The measurement space is comprised of the plane and interplane slices stacked one on top of the other where each plane is divided into an array of measurement positions. Each measurement position is referred to as a pixel location. Each pixel measurement position is located in the measurement space according to a three-dimensional coordinate system (x, y, z). Each plane has an identical array of pixel locations which are known.

For simplicity of illustration, a coincidence line is shown in FIG. 6 contained in the top plane slice together with the positional uncertainty function for a detected annihilation. As previously discussed, each detected annihilation outputted by the group-pair processors 20 includes the geometrical location of each detected annihilation, along with the angle θ of the coincidence line with the interplane slices and the attenuation-uniformity coefficient to be applied to this annihilation. (For the coincidence line shown in FIG. 6, the angle θ is zero.) The function of the attenuation-uniformity coefficient is to weight the positional uncertainty function to obtain a distributed contribution that is added to the image data at a pluality of pixel locations lying closest to the coincidence line which are spanned by non-zero values of the weighted uncertainty function rather than having the detected annihilation summed as a single event at a single pixel location. This is illustrated in FIG. 6 by the distributed contributions to those pixel locations lying closest to the coincidence line. By weighting the positional uncertainty function according to the attenuation-uniformity coefficient, the higher order coincidences b, c, d, e, can be used properly.

In the more geometrically complex case where a cross-coincidence line is involved, the various pixel locations that will receive a distributed contribution will lie on different image slices, but the principle is the same. That is, each pixel location on each image slice is determined which is closest to the coincidence line and the contribution calculated from the weighted uncertain function along the cross-coincidence line will be summed with the data for that measurement pixel location.

Figure 7:
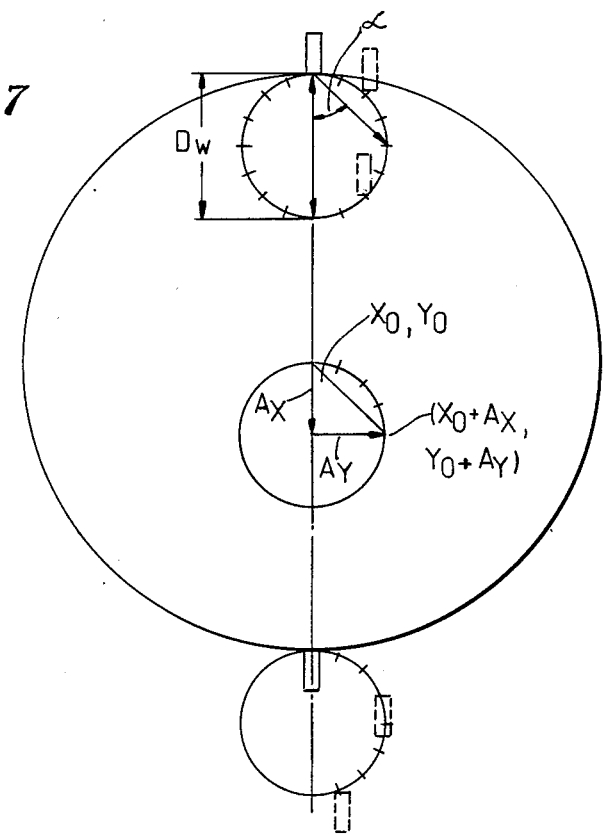
FIG. 7 is an illustration of the wobbling of the detector gantry according to the present invention.

It is a well-established fact that uniform sampling and uniform response of the detectors is required for the reconstruction of an image. However, in practice, this is difficult to accomplish since 400 or more detectors in a camera cannot be expected to have similar detection efficiency or timing capabilities. Corrections are possible in the group-pair 20 and slice processors 28 as the data are collected such that the reconstruction algorithm is presented with data which are fairly close to uniform for each detector. Thus, it is possible to correct for some amount of difference in sampling in uniformity without causing major artifacts in the images. An additional technique for increasing the sampling of the area of reconstruction involves wobbling the detector gantry while the scintillations measurements are being made. The term "wobble" refers to rotating the entire detector gantry such that each detector traces a circular motion. FIG. 7 is an illustration of the wobble for two detectors located 180° apart on a single ring where the wobble is circular in character. While a circular wobble is shown and described, as long as the position of the detectors is known so that their geometrical position can be calculated, the motion can follow any desired path. It has been found that a circular motion results in the best increase in sampling of the area of interest.

Referring now to FIG. 7, the present invention digitizes the wobble into one hundred and forty-four intervals. The effect of wobbling the detectors is apparent, the area of reconstruction will be sampled more uniformly and more completely than when the detectors are in a fixed position. For a wobble diameter of 19.8 mm, the error caused in sampling of a uniform source 50 cm in diameter is less than 1% for the uniformity in the field of view. Since the wobble of the detector gantry 10 is known, the position of each detected annihilation in the measurement space as defined by FIG. 6, can be precisely determined.

Figure 8:
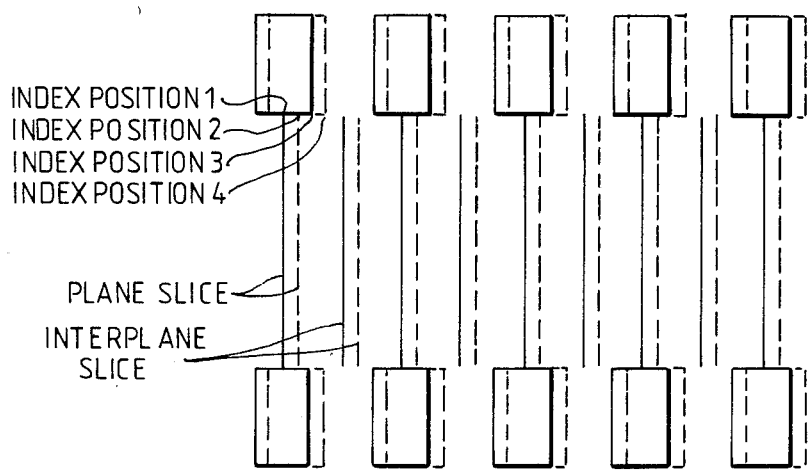
FIG. 8 is an illustration of the effect of indexing of the detector gantry longitudinally with respect to the area of reconstruction on the generation of the interplane slices.

In order to further improve the sampling for the cross-coincidence lines and to completely sample the region of interest between the detectors, the detector gantry can be moved along the z axis or perpendicular to the plane of image reconstruction. This longitudinal indexing of the detector gantry 10 with respect to the area of reconstruction is illustrated in FIG. 8 in which four translation steps are used. Four translation steps have been found to be sufficient to uniformly sample the region between the plane slices defined by the detector rings. Each indexed position is approximately ¼ of the separation between the of detectors.

Referring to FIG. 8, the nine plane and interplane slices shown as solid lines are obtained when the ganty 10 is in the left most position. When the gantry is indexed to the right ¼ of the separation distance between detectors, the nine plane and interplane slices will pass through the area of interest in the positions as shown by the dotted lines. This process is repeated at each index position with a resulting increase in the coverage of the area of interest.

For the presently preferred embodiment, slice thickness is defined to be the same as the translation distance along the z axis. Each slice is processed independently for a total of twenty slices within the area of reconstruction. These twenty slices can be combined to form 10 slices which are 10.8 mm wide or seven slices which are 16.2 mm wide, etc. This combination of slices can be achieved at a later time after the images are reconstructed and at the discretion of the operator.

Summarizing the present invention, a multiple-ring positron-emission detection camera is disclosed in which the cross-coincidence lines between detectors on different rings are used with the time-of-flight information of the detected annihilations to accurately determine the geometrical position of the annihilations within the area of reconstruction. The nearest position on the nearest plane or interplane slice to the position of each annihilation is determined. Based on the positional uncertainty function for the detector system and an attenuation-uniformity coefficient, a contribution of each annihilation to those measurement positions which lie closest to the coincidence line where a non-zero contribution from the annihilation is obtained is added to the data of the measurement position. In this manner, the cross-coincidence lines between all of the rings will contribute to the image data thereby to increase the radiation detection efficiency of the camera.

In describing the invention, reference has been made to its preferred embodiment. However, those skilled in the art and familiar with the disclosure of the invention may recognize additions, deletions, substitutions or other modifications which would fall within the purview of the invention as defined in the appended claims.

What is claimed is:

1. A method of improving the radiation detection efficiency of a time-of-flight positron emission camera having a plurality of detector rings positioned side-by-side around an area of reconstruction, each ring having a circumference and each containing a plurality of scintillation detectors which are positioned to its circumference and are pointed at the area of reconstruction to detect radiation therefrom, each detector in each ring having an opposed detector on each ring positioned 180° therefrom where each detector together with an opposed detector defines a detector pair for detecting the two photons emitted within a coincidence line defined by the coincident solid angle cylindrical line connecting each detector from a positron-electron annihilation occurring in the area of reconstruction, each detector ring defining a plane slice through the area of reconstruction with an interplane slice defined as all equidistant points located between any two adjacent detector rings measured from either plane slice, and where each slice has an array of measurement positions, the method comprising the steps of:

(a) determining the time-of-flight (TOF) of each annihilation detected along a coincidence line;
(b) determining the position of each annihilation detected in each plane slice from the TOF of the annihilations detected along coincidence lines between detectors on the ring defining the plane slice;
(c) determining from the TOF the position for each annihilation detected along each coincidence line involving detectors on different rings; and
(d) forming the total detected annihilations which have occurred at each measurement position in each plane and interplane slice by
  (i) summing with the annihilations detected in each measurement position from coincidence lines in each plane slice the annihilations detected on coincidence lines involving detectors on different rings where the position of the annihilations so detected are within a predetermined distance of the measurement position in the plane, and (ii) summing for each measurement position on an interplane slice the annihilations detected on coincidence lines involving detectors on different rings where the position of the annihilations so detected are within a predetermined distance of the measurement position in the interplane thereby increasing the detection efficiency of the camera.

2. The method of claim 1 wherein the step of measuring the TOF of each annihilation along a coincidence line comprises measuring the time difference between the simultaneous detection of radiation from an annihilation by each detector in the detector pair where simultaneous detection occurs when the detected radiation in one detector of the pair is within a predetermined time interval of the detection of radiation in the other detector.

3. The method of claim 1 wherein the predetermined time interval between the detections of an annihilation by both the detectors in a detector pair is controlled according to the size of the area of reconstruction.

4. The method of claim 3 where the predetermined time interval is 8 nanoseconds or less.

5. The method of claim 2 wherein the step of determining the position of an annihilation along a coincidence line comprises solving the following equation, $$x = \left[ \frac{(TOF) \cdot (c) + D}{2} \right] + \Delta,$$

where x is the distance measured from one of the detectors in the detector pair defining the coincidence line, c is the velocity of light, D is the length of the coincidence line between the detectors, and $\Delta$ is the delay variations due to the propagation of signals in the detector electronics.

6. The method of claims 1, 2 or 5 wherein the step of forming the total detected annihilations at each position in each plane and interplane slice includes the steps of:

(a) converting the position of each detected annihilation along a coincidence line between detectors on different rings into orthogonal components comprising (i) a perpendicular distance of the annihilation as measured from the plane slice which includes one of the detectors defining the coincidence line, the detector used in defining the plane being a reference detector and the plane being a reference plane for that annihilation, and (ii) a horizontal distance as measured from the reference detector of the annihilation along a line projected by the cross-coincidence line onto the reference plane;

(b) determining for each annihilation the plane or interplane slice that is nearest the annihilation detected along a coincidence line between detectors on different rings as measured by the perpendicular distance from the reference plane of the annihilation; and (c) determining the measurement position in the nearest plane determined in step (b) to the annihilation for summing therewith, the measurement position determined from the horizontal distance determined in step (a), thereby including the annihilation detected by detectors on different rings into the total detected annihilations in the plane and interplane slices.

7. The method of claim 6 wherein the step of converting the position of an annihilation along a coincidence line between detectors on different rings comprises the steps of:

(a) solving the following equation for the perpendicular distance z, $$z = x \sin \theta,$$

where x is the distance of the annihilation along the coincidence line from the reference detector in the detector pair defining the coincidence line, $\theta$ is the angle measured between the coincidence line and the reference plane, and z is the perpendicular distance measured from the reference plane to the annihilation; and (b) solving the following equation for the horizontal distance d from the reference detector as measured in the reference plane containing the reference detector, $$d = x \cos \theta,$$

8. The method of claim 1 further including the step of generating a two-dimensional image of the area of reconstruction as a plane slice through the area of reconstruction from the number of annihilations obtained at each measurement position in a plane (a) defined by the plane containing all the detectors in a detector ring, or (b) defined by all the measurement positions contained in an interplane slice.

9. The method of claim 1 further including the step of increasing the sampling of the area of reconstruction at a fixed position of the detector rings relative to longitudinal movement along the area of reconstruction by wobbling the detector rings such that the position of each detector relative to the area of reconstruction varies in a known manner.

10. The method of claims 1 or 9 further including the steps of:

(a) indexing in predetermined increments the plurality of detector rings in a longitudinal direction relative to the area of reconstruction; and (b) repeating at each index position the steps of detecting the annihilations along all coincidence lines between the plurality of detectors to obtain the annihilations detected at each measurement position on the plane and interplane slices thereby to increase the sampling of the area of reconstruction without an increase in the number of detector rings.

11. The method of claim 6 wherein the location of each annihilation along a coincidence line has a location uncertainty characterized by a positional uncertainty function along the coincidence line where the peak of the function occures at the most likely position for the annihilation, the step of forming the total detected annihilation which have occurred at each measurement position in each plane and interplane slice further including the steps of:

(a) determining the orthogonal components for a plurality of spaced locations along a coincidence line relative to the most likely position of the annihilation which are spanned by the positional uncertainty function centered at the most likely position of the detected annihilation;

(b) for each location determined in step (a), determine a partial annihilation contribution according to the value of the positional uncertainty function at that location; and (c) summing each partial annihilation contribution at each spaced location with the measured annihilations at the nearest measurement location on the nearest plane or interplane slice to the spaced location.

12. The method of claim 11 wherein the step of determining a partial annihilation contribution for the spaced locations along a coincidence line includes the step of weighting the positional uncertainty function by an attenuation uniformity coefficient so that the total distributed contributions summed into the image data is equal to one annihilation.

13. A method of improving the radiation detection efficiency of a time-of-flight positron emission camera having a plurality n of detector rings positioned side-by-side around an area of reconstruction, each ring having a circumference and each containing a plurality of scintillation detectors which are positioned around its circumference to detect radiation occurring from the area of reconstruction along a coincidence line defined by the coincidence solid angle cylindrical line connecting a detector with another detector, the plurality of detectors on the detector rings are divided into a plurality of detector groups, each group having m×n detectors where m represents a number of adjacent detectors on the same ring, the plurality of detector groups defining therebetween a plurality of group coincidence line where each group coincidence line connects a first and a second group and includes the coincidence lines between each detector, taken one at a time, in the first group and every detector in the second group, each detector in the first group together with a detector in the second group defining a detector pair for detecting the two photons emitted along the coincidence line therebetween, each detector ring defining a plane slice through the area of reconstruction with an interplane slice defined as all equidistant points located between any two adjacent detector rings as measured from either plane slice and where each slice has an array of measurement positions included in the area of reconstruction, the method comprising the steps of:

(a) determining the time-of-flight (TOF) of the annihilations detected along the group coincidence lines, the TOF determination including a determination of which coincidence line in the group detected the annihilation;

(b) determining from the TOF the location of each detected annihilation along a coincidence line;

(c) determining for each detected annihilation location the nearest measurement position on the nearest plane or interplane slice to the location of the annihilation; and (d) forming the total detected annihilations for each measurement position in each plane and interplane slice by summing each detected annihilation with the number of annihilations already obtained at the nearest measurement position to the location of the annihilation, thereby to obtain a greater detection efficiency for the camera.

14. The method of claim 13 wherein the step of measuring the TOF of each annihilation detected along a group coincidence line between a first and a second group defining the group coincidence line comprises the steps of:

(a) sequentially scanning each detector in the first group to determine if a detector is generating an active signal indicative of the detection of a photon coming from the area of reconstruction;

(b) initiating a time interval measurement in response to the detection of an active signal from the first group;

(c) sequentially scanning each detector in the second group to determine if a detector is generating an active signal indicative of the detection of a photon coming from the area of reconstruction;

(d) terminating the time interval measurement in response to the detection of an active signal from the second group, the resulting measured time representing the TOF of a detected annihilation if the time interval is less than a predetermined amount; and (e) indicating for each detected annihilation the two detectors which generated the TOF interval thereby indicating the coincidence line along which the annihilation was detected.

15. The method of claim 14 wherein the predetermined time interval for the detection of an annihilation is determined by the size of the area of reconstruction.

16. The method of claim 14 wherein the step of determining the position of an annihilation along a coincidence line comprises solving the following equation, $$x = \left[ \frac{(TOF)(c) + D}{2} \right] + \Delta,$$

where x is the distance measured from one of the detectors in the detector pair defining the coincidence line, c is the velocity of light, D is the length of the coincidence line between the detectors, and $\Delta$ is the electronic delay between detectors.

17. The method of claim 16 wherein the step of determining for each detected annihilation the nearest measurement position on a plane or interplane slice includes the steps of:

(a) converting the position of each detected annihilation along a coincidence line into orthogonal components comprising (i) a perpendicular distance of the annihilation as measured from the plane slice which includes one of the detectors defining the coincidence line, the detector used in defining the plane slice being a reference detector and the plane being a reference plane for the annihilation, and (ii) a horizontal distance of the annihilation from the reference detector in the reference plane as measured along a projection of the coincidence line onto the reference plane;

(b) determining for each annihilation the plane or interplane slice that is nearest the annihilation as measured by the perpendicular distance from the reference plane of the annihilation; and (c) determining from the horizontal distance determined in step (a) the measurement position in the nearest plane, determined in step (b), to the annihilation.

18. The method of claim 17 wherein the step of converting the position of an annihilation along a coincidence line into orthogonal components comprises the steps of:
(a) solving the following equation for the perpendicular distance z, $$z = x \cdot \sin \theta,$$

where
x is the distance of the annihilation along the coincidence line from the reference detector in the detector pair defining the coincidence line,
$\theta$ is the angle measured between the coincidence line and the reference plane, and
z is the perpendicular distance measured from the reference plane to the annihilation; and
(b) solving the following equation for the horizontal distance d from the reference detector as measured in the reference plane containing the reference detector, $$d = x \cdot \cos \theta.$$

19. The method of claim 13 further including the step of generating a two-dimensional image of the area of reconstruction as a plane slice from the number of annihilations obtained at each measurement position in a plane
(a) defined by the plane containing all the detectors in a detector ring, or
(b) defined by all the measurement positions contained in an interplane slice.

20. The method of claim 13 further including the step of increasing the sampling of the area of reconstruction at a fixed position of the detector rings by wobbling the detector rings such that the position of each detector relative to the area of reconstruction varies in a known manner.

21. The method of claims 13 or 20 further including the steps of:
(a) indexing in a longitudinal direction relative to the area of reconstruction in predetermined increments the plurality of detector rings; and
(b) repeating at each index position the steps of detecting the annihilation along coincidence lines between detectors to obtain the image data at each measurement position on the plane and interplane slices thereby to increase the sampling of the area of reconstruction without an increase in the number of detector rings.

22. The method of claim 13 wherein the location of each annihilation along a coincidence line has a location uncertainty characterized by a positional uncertainty function along the coincidence line where the peak of the function occures at the most likely position for the annihilation, the step of forming the total detected annihilation which have occurred at each measurement position in each plane and interplane slice further including the steps of:
(a) determining the orthogonal components for a plurality of spaced locations along a coincidence line relative to the most likely position of the annihilation which are spanned by the positional uncertainty function centered at the most likely position of the detected annihilation;
(b) for each location determined in step (a), determine a partial annihilation contribution according to the value of the positional uncertainty function at that location; and
(c) summing each partial annihilation contribution at each spaced location with the measured annihilations at the nearest measurement location on the nearest plane or interplane slice to the spaced location.

23. The method of claim 22 wherein the step of determining a partial annihilation contribution for the spaced locations along a coincidence line includes the step of weighting the positional uncertainty function by an attenuation uniformity coefficient so that the total distributed contributions summed into the image data is equal to one annihilation.

24. A time-of-flight positron emission camera having an improved radiation detection efficiency for detecting the photons emitted by an electron-positron annihilation along a line of coincidence and for locating the annihilation within an area of reconstruction where the location of each annihilation along a coincidence line has a location uncertainty defined by a location uncertainty function, said camera generating two-dimensional images as plane slices through the area of reconstruction where each slice comprises a plurality of measurement positions, the camera comprising:
(a) a plurality n of detector rings positioned side-by-side around the area of reconstruction, each said ring containing a plurality of scintillation detectors positioned around the ring for detecting radiation from the area of reconstruction along coincidence lines where a coincidence line is defined by the coincidence solid angle cylindrical projection from one detector to another within which an annihilation may be detected, and where
(i) the plurality of detectors on the detector rings are divided into detector groups, each group having $m \times n$ detectors where m represents a number of adjacent detectors on the same ring, the plurality of detector groups defining therebetween a plurality of group coincidence lines where each group coincidence line connects a first and a second group and includes the coincidence lines between each detector, taken one at a time, in the first group and every detector in the second group, each detector in the first group together with a detector in the second group defining a detector pair for detecting the two photons emitted along the coincidence line therebetween, and
(ii) each detector ring defines a plane slice through the area of reconstruction with an interplane slice defined as all equidistant point located between any two adjacent detector rings as measured from either plane slice and where each slice has an array of measurement points included in the area of reconstruction;
(b) a plurality of time-of-flight detectors for measuring the time difference between the simultaneous detection of the photons from an annihilation by a first and a second detector group along a group coincidence line where simultaneous detection occurs when the detected photon by one detector in the first group is within a predetermined time interval of the detection of a photon by another detector in the second group;

(c) a plurality of group-pair processors, one associated with each of said time-of-flight detectors, for determining the location of each detected annihilation relative to the nearest measurement position in the slice nearest to the location of the annihilation;

(d) a plurality of slice processors responsive to said group-pair processors for generating the number of annihilation detected at each measurement position in each plane and interplane slice where each annihilation produces a partial contribution to the number of detected annihilations at a plurality of measurement positions which lie closest to the coincidence line of the detected annihilation in accordance with the location uncertainty function; and (e) a display means for displaying a two-dimensional image of the area of reconstruction as a plane slice through the area of reconstruction from the number of annihilation obtained at each measurement position in a plane or interplane slice.

25. The camera of claim 24 further including a master processors responsive to said slice processors, said master processor providing controlled, system calibration and an interface with an operator.

26. The camera of claims 24 or 25 further including means for displaying a three-dimensional image of the area of reconstruction from the annihilations detected at measurement positions in the plane and interplane slices.

27. The camera of claim 24 wherein each said time-of-flight detector includes:

(a) a first encoder means associated with a first detector group for detecting when a detector in the first detector group has detected a photon from an annihilation, said first encoder means generating a start conversion signal in response to a detected photon;

(b) a second encoder means associated with a second detector group, said first and second detector groups defining therebetween a group coincidence line for detecting when a detector in the second detector group has detected a photon from an annihilation, said second encoder means generating a stop conversion signal in response to a detected photon; and (c) a time-to-digital converter responsive to the start and stop conversion signals for measuring the time difference between the detection of a photon by the first group and the detection of a photon by the second group, the time difference representing the time-of-flight of an annihilation along the coincidence line between the detectors which detected the photons in said first and second groups if the time difference is less than a predetermined amount.

28. The camera of claim 27 wherein the time-of-flight detector further includes a first-in first-out buffer memory for storing the measured time-of-flight for each detected annihilation.

29. The camera of claim 24 further including means for wobbling during detection of the annihilations said plurality of detector rings such that the position of each detector relative to the area of reconstruction varies in a known manner thereby increasing the sampling of the area of reconstruction.

30. The camera of claims 24 or 29 further including means for indexing said plurality of detector rings longitudinally relative to the area of reconstruction in predetermined increments thereby increasing the number of measurement slices through the area of reconstruction.

31. The camera of claim 24 wherein said plurality of group-pair processors output for each location of each detected annihilation the angle of the coincidence line to the plane slices and an attenuation-uniformity coefficient whereby said slice processors weight the location uncertainty function to obtain partial distributed annihilations contributions along the coincidence line to be summed into the image data for the measurement positions closest to the distributed contribution locations along the coincidence line, the total of the distributed contributions equally one annihilation.

32. A time-of-flight positron emission camera having a plurality of detector rings positioned side-by-side around an area of reconstruction, each detector ring defining a plane slice through the area of reconstruction and each pair of adjacent rings having at least two interplane slices defined therebetween through the area of reconstruction, each ring having a plurality of sincintillation detectors with each detector having an opposed detector on its ring together defining a detector pair having a coincidence line therebetween for detecting the two photons emitted from a positron-electron annihilation occurring the plane slice of the detectors, and where detector pairs formed from detectors on different rings have cross-coincidence lines therebetween also for detecting annihilations in the area of reconstruction, the camera including a means for increasing the radiation detection efficiency of the camera by determining from time-of-flight information the location of each detected annihilation in the area of reconstruction obtained along cross-coincidence lines and including these detected annihilations in the image data of the plane or inter-plane slice closest to the location of the detected annihilation.

33. The camera of claim 32 wherein the location of each detected annihilation along a coincidence or cross-coincidence line has a location uncertainty characterized by a positional uncertainty function along the line where the peak of the function occurs at the most likely position for the annihilation, said means for increasing the radiation detection efficiency further including a means for determining weighted orthogonal components for a plurality of spaced locations along a coincidence or cross-coincidence line relative to the most likely position of the detected annihilation, which locations are spanned by the positional uncertainty functions centered at the most likely position of the detected annihilation, the weighted orthogonal components representing a partial annihilation contribution according to the value of the positional uncertainty function at that location, said means including each partial annihilation contribution at each spaced location in the image data at the nearest measurement location on the nearest plane or inter-plane slice to the spaced location.

34. The camera of claim 32 further including a means for increasing the number of slices through the area of reconstruction by indexing the plurality of detector rings, a determined amount, in a direction along the line passing through the center of each detector ring.

35. The camera of claims 32 or 34 further including a means for increasing the sampling of the area of reconstruction by wobbling the plurality of detector rings in a prescribed path relative to the area of reconstruction.

36. A time-of-flight positron emission camera having at least three detector rings positioned side-by-side around an area of reconstruction for creating images from data obtained from the area of reconstruction, each ring having a plurality of scintillation detectors, and each detector ring defining a plane slice through the area of reconstruction, the camera including a means for improving the radiation detection efficiency of the camera by including each detected positron-electron annihilation located from time-of-flight information derived from detectors located on different rings into the image data for the plane slice closest to the detected annihilation.

37. The camera of claim 36 further including a means for forming an inter-plane slice between each adjacent pair of detector rings, said means for improving the radiation detection efficiency cumming each detected annihilation from detectors located on different rings into the image data for the plane or inter-plane slice closest to the detected annihilation.

38. The camera of claim 37 further including a means for increasing the number of image slices through the area of reconstruction by indexing the plurality of detector rings a determined amount in an axial direction.

39. The camera of claims 37 or 38 further including a means for increasing the sampling of the area of reconstruction by radially wobbling the plurality of detector rings in a prescribed path relative to the area of reconstruction.

40. The camera of claim 37 wherein the location of each detected annihilation along a coincidence or cross-coincidence line has a location uncertainty characterized by a positional uncertainty function along the line where the peak of the function occurs at the most likely position for the annihilation, said means for increasing the radiation detection efficiency further including a means for determining weighted orthogonal components for a plurality of spaced locations along a coincidence or cross-coincidence line relative to the most likely position of the detected annihilation, which locations are spanned by the positional uncertainty functions centered at the most likely position of the detected annihilation, the weighted orthogonal components representing a partial annihilation contribution according to the value of the positional uncertainty function at that location, said means including each partial annihilation contribution at each spaced location in the image data at the nearest measurement location on the nearest plane or inter-plane slice to the spaced location.

* * * * *

UNITED STATES PATENT OFFICE  Page 1 of 2
CERTIFICATE OF CORRECTION

Patent No. __4,559,597__        Dated __December 17, 1985__

Inventor(s) __Nizar A. Mullani__

It is certified that error appears in the above-identified patent and that said Letters Patent are hereby corrected as shown below:

Column 2, line 61, delete "ano" and insert -- and --

Column 3, line 32, change "byside" to -- by-side --

Column 4, line 24, change "positronelectron" to -- positron-electron --

Column 12, line 2, delete the text after "side-by-side" through Column 12, line 35, ending with the word "described" and insert this text in Column 13, line 2, after the second occurrence of "other"

Column 12, line 67, change "threedimensional" to -- three-dimensional --

Column 15, line 58, delete "ganty" and insert -- gantry --

Column 18, line 28, in the formula, delete the " , " and insert -- . --

Column 24, line 25, after "occurring" insert -- in --

UNITED STATES PATENT AND TRADEMARK OFFICE
CERTIFICATE OF CORRECTION

PATENT NO. : 4,559,597

DATED : December 17, 1985

INVENTOR(S) : Nizar A. Mullani

It is certified that error appears in the above-identified patent and that said Letters Patent is hereby corrected as shown below:

Column 25, line 14, delete "cumming" and insert
-- summing --.

Signed and Sealed this

Twenty-second Day of April 1986

[SEAL]

Attest:

DONALD J. QUIGG

Attesting Officer

Commissioner of Patents and Trademarks